United States Patent [19]
Holmes

[11] Patent Number: 4,760,842
[45] Date of Patent: Aug. 2, 1988

[54] THERAPEUTIC TRACTION DEVICE

[76] Inventor: Kenneth E. Holmes, 16871 Saybrook La., Huntington Beach, Calif. 92649

[21] Appl. No.: 10,919

[22] Filed: Feb. 5, 1987

[51] Int. Cl.$^4$ .............................................. A61F 5/00
[52] U.S. Cl. ....................................... 128/75; 128/69
[58] Field of Search ............... 128/75, 68, 68.1, 69, 128/70, 24, 24.1

[56] References Cited

U.S. PATENT DOCUMENTS 3,421,163 1/1969 Stoughton ............................ 128/68
3,842,453 10/1974 Redfield ............................... 128/68

FOREIGN PATENT DOCUMENTS 2506151 11/1982 France ................................ 128/68

Primary Examiner—Edgar S. Burr
Assistant Examiner—Huong Q. Pham
Attorney, Agent, or Firm—Knobbe, Martens, Olson & Bear

[57] ABSTRACT

A support in the form of a rigid plastic container is shaped to conform to the back of a person's neck and suitably support the neck and head in a manner to provide traction on the spine. By putting hot water in the container, the neck is conveniently heated at the same time. A groove in the upper surface of the support is located to receive spinal vertebrae to minimize direct pressure in that area.

12 Claims, 1 Drawing Sheet

THERAPEUTIC TRACTION DEVICE

FIELD OF THE INVENTION

This invention relates to therapeutic devices for the human body and particularly to a device for providing traction on a person's spine.

BACKGROUND OF THE INVENTION

Literally millions of people suffer from back and spinal problems. Much effort and money has been expended in treating and trying to prevent ailments and discomfort of this type, with varying degrees of success. In addition to the discomfort, chronic back ailments cause a great deal of absenteeism from work. Further, many people ultimately require surgery to gain some relief, and some people become permanently incapacitated. In addition to the expense for the treatment of back ailments, there is also the enormous economic loss from people unable to work, as a result of back ailments. Accordingly, a great need exists for any practical improvements in this area.

One commonly employed technique for providing some improvement to spinal problems is to position a rolled towel under a person's neck so that the weight of the head is supported by the neck and so that some traction or elongating or stretching force is applied to the person's spine. This treatment applied for a limited period of time appears to provide relief for some people by relieving the normal vertical load that is applied to a patient's spine while standing or sitting. Related to this, it is understood that the ancient Chinese have used bamboo logs for this purpose. These approaches have their shortcomings and improvements are needed.

SUMMARY OF THE INVENTION

Briefly stated, the invention comprises a rigid support to be placed under a person's neck so as to take the load off the head. The device is provided with curved surfaces to smoothly and comfortably distribute the forces on the neck in a manner to provide traction or an elongating force on the person's spine. Preferably the support has a curved groove or recess that is positioned to receive and be aligned with the neck vertebrae so as to provide comfort in that area.

Preferably the support is hollow and is provided with an opening to the interior, together with a closure so that the support forms a container which can be filled with hot water before being placed beneath the person's neck so as to provide a heated traction producing device. The device should normally be used for no more than a limited period of time, such as about the length of time it takes the water to cool. Thus, the container-type support becomes in effect a self timer.

The rigid support has been found to be much more effective than the folded rolled towel technique because of the firmness of the support. While the rigid device is surprisingly comfortable, a degree of additional comfort is provided by placing a layer of fabric over the areas of the support being engaged by the person's neck. This is conveniently accomplished by providing a stretchy-type fabric in a tubular form that can be simply slipped onto either end of the support. The fabric snugly conforms to the shape of the support, and can be conveniently removed and repositioned for cleaning.

DETAILED DESCRIPTION

The therapeuctic device of the invention includes a hollow container 10 having an inlet on one end closed by a removable plug 12, and a fabric covering 14 extending over the majority of the container.

Figure 1:
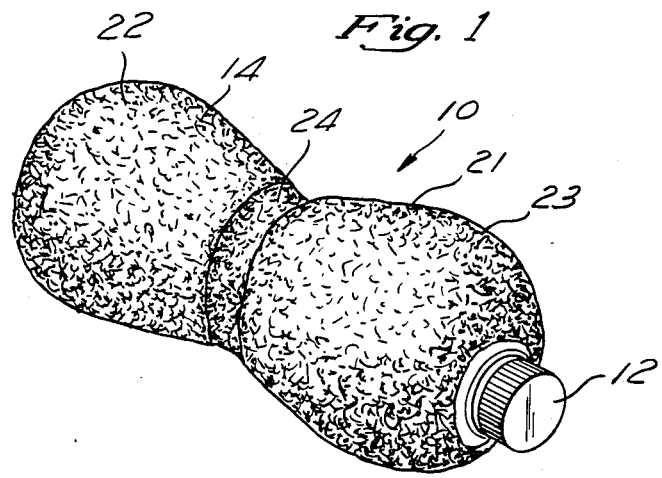
FIG. 1 is a perspective view of the traction device of the invention.
Figure 2:
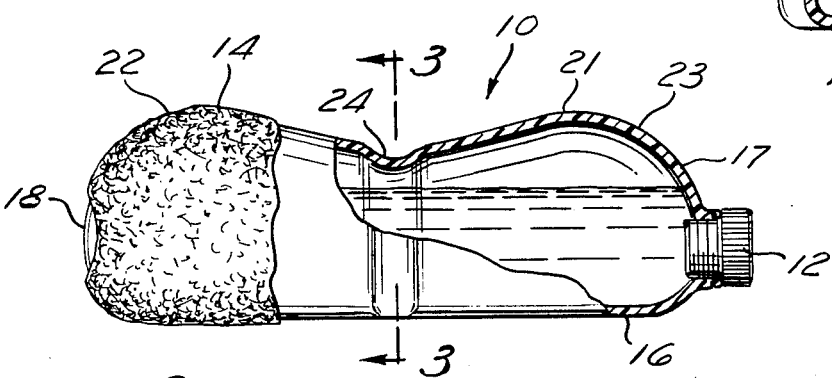
FIG. 2 is a side elevational view of the device with a portion of the cover cutaway and with a portion of the container in cross section.

The container 10 has a flat bottom wall 16 for resting on a support surface and smoothly curving side walls 17, 18, 19 and 20 and top wall 21. The side walls extend generally vertically and then blend smoothly into the curved upper wall 21. The container includes two bulbous end portions 22 and 23 that have convex or outwardly curved surfaces. These convex portions curve smoothly to a concave central area or portion, which terminates in a shallow concave groove 24 around the midsection of the side and top walls of the container, as best seen in FIGS. 1 and 2. The bulbous end portions 22 and 23 include areas that slope towards the central portion and are shaped to smoothly, engage the sides of a person's neck, as may be appreciated from the view of FIG. 2. The shallow central groove is provided to receive spinal processes so as to relieve pressure on the spine.

Figure 3:
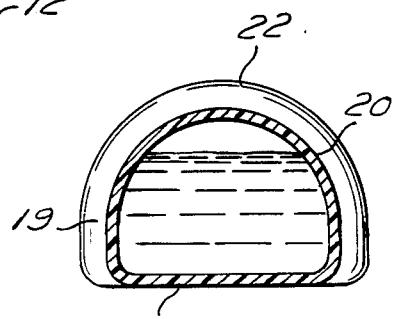
FIG. 3 is a cross-sectional view on line 3—3 of FIG. 2.
Figure 4:
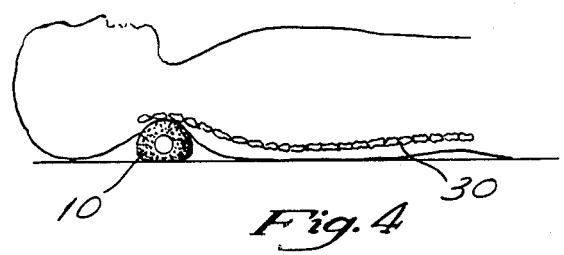
FIG. 4 is a schematic view illustrating the device in use.

The top wall 21 and the side walls 19 of the container are smoothly rounded from front to back, as best seen from FIGS. 3 and 4 so as to conform to the back lower portion of a person's head and the portion of a person's body adjoining the neck to the shoulder area.

The container is preferably made of a rigid plastic that provides a desired firm support. Although the device can be used without a cover, it has been found that the fabric cover 14 adds comfort to the feel of the user when the neck is placed in contact with the device. The cover is conveniently made of a stretchy fabric so that it will conform to the container. It is preferably made in a tubular form with an elastic on either end, such that it can be slipped off and on to the container with ease, thereby facilitating cleaning of the cover as needed.

As can be seen from FIG. 4, the height of the device is sufficient to cause the weight of the person's head and neck to be primarily supported on the device. The head can be lightly touching the floor or other support surface, or can be slightly spaced from the support, as desired or as prescribed by a person's doctor. The intent is that the cantilever support of the head provides a stretching or traction action on the person's spine 30, which is the desired effect.

In a preferred form of the invention, the device is about 4 inches in height at the shallow central portion and about 5 inches in height at the peak of the bulbous end portions. The length of the device is preferably about 9 inches. Such dimensions have been found to be adequate to fit most people, but of course, these dimensions may be varied for different size people. Nevertheless, the proportions between the central section and the end portions should preferably be maintained by the above indicated dimensions. That is, the height of the central section is preferably only about 80 to 90% of the height of the bulbous side portions. By making the device a minimum height, it can be conveniently raised as desired by inserting a flat spacer beneath the device.

The shallow central groove is preferably formed on a radius of about ½ inch and extends about ⅜ inch in width, as viewed in FIG. 2.

It has been found that heat on the neck also provides some additional therapeutic effect. Thus, the container may be filled with hot water when it is to be used. Most people find that 15 or 20 minutes of use per day provides considerable relief. The hot water is a convenient timer for that purpose in that the water cools considerably after 15 or 20 minutes of use, to indicate this cooling. Some users report a feeling of relaxation that helps then sleep after use of the device. The warmth is also conducive to relaxation.

It has also been found that with hot water a container made of a desired plastic having a wall thickness of about ⅛ inch will remain rigid to properly elevate the head, but will deform slightly to conform to the back of the head and shoulder area.

What is claimed is:

1. A therapeutic traction device comprising:
   a rigid support adapted to be placed beneath a person's neck while the person is lying on his back on a support surface;
   said support including rigid side walls and a similarly rigid top wall having a central area that is engaged by the person's neck and an end portion at each end of said central area, said central area being recessed relative to said end portions, the height of said support being sufficient to raise the person's head so that the weight is primarily on the neck and a traction effect is applied to the spine; and
   said recessed central area including a shallow groove adapted to be aligned with and receive a portion of the person's spine to relieve the direct pressure on the spine.

2. The device of claim 1, wherein the surface of the recessed central area is concave upwardly and is smoothly curved so that the load on the patient's neck is smoothly and comfortably distributed on the neck.

3. The device of claim 2 wherein said support includes:
   a sidewall facing the person's head that curves smoothly downwardly from said central area to cradle the portion of the person's neck that blends into the lower back portion of the head; and
   said support includes a sidewall facing the person's back that curves smoothly downwardly from said top wall central area; and
   said groove continues from said central area into said sidewall facing the person's back.

4. The device of claim 3 wherein said end portions are bulbous portions which have a smoothly curved upper surface higher than said central area, that slopes downwardly to and blends into said central area to cradle the side rear portions of the neck.

5. The device of any of claims 1-4 wherein said support is hollow and said support includes a closable opening through which hot water may be introduced into the support so as to heat the neck when the said device is in use.

6. The device of any of claims 1-4 including a fabric cover that extends over said central area.

7. The device of claim 1 wherein the support is hollow and a closable opening is provided in the support to permit hot water to be contained in it so that the person's neck is heated when the device is used.

8. The device of claim 7 including a layer of fabric positioned on the surface of the support to be engaged by the person's neck.

9. The device of claim 8 wherein said fabric is stretchy and is in the form of a tubular element that can be slipped over the support and will snugly fit the support.

10. The device of claim 9 wherein an open end of the tubular fabric element includes an elastic which causes the fabric to snugly engage a lateral end of the support.

11. A method of providing traction on a person's spine comprising the steps of positioning beneath a person's neck while the person is lying on his back, a support which is uniformly rigid throughout and smoothly curved to provide an end portion at each end and a recessed central area between said end portions to comfortably engage and distribute the weight of the person's neck and head on the support and is also smoothly curved on the sides to cradle the sides of a person's neck and to cradle the portion of the neck that blends into the rear back portion of a person's head; and relieving pressure along the person's spine by providing a groove in the recessed central area of said support, said groove being aligned to receive the spinal vertebrae when the neck is placed on the support.

12. The method of claim 11 wherein said support is hollow and includes a closable opening in one of its end portions so that the support forms a container; and
   including the step of filling the container with hot liquid before said positioning step so that the person's neck is heated by the device when it is beneath the person's neck.

* * * * *